United States Patent [19]

Bennett

[11] Patent Number: Plant 6,788

[45] Date of Patent: May 9, 1989

[54] MINIATURE ROSE PLANT, NAMED 'SWEET PICKINS'

[75] Inventor: Cecilia L. D. Bennett, Chula Vista, Calif.

[73] Assignee: Susan Mae O'Brien, Chula Vista, Calif.

[21] Appl. No.: 151,253

[22] Filed: Feb. 1, 1988

[51] Int. Cl.[4] ..... A01H 5/00

[52] U.S. Cl. ..... Plt./9

[58] Field of Search ..... Plt./9

*Primary Examiner*—James R. Feyrer

[57] ABSTRACT

The subject of the present disclosure is a new and distinct variety of miniature rose plant, named 'Sweet Pickins', which is characterized by its pale pink blooms, ranging from near French Rose to near Venetian Pink. The blooms are usually borne one to a stem with hybrid tea form. The bush is vigorous, well-branched and produces a moderate to heavy quantity of blooms.

1 Drawing Sheet

1

The present invention relates to a new and distinct variety of a hardy, dwarf, bush plant of the miniature class; the variety being primarily characterized as a light pink.

The variety is further characterized by:

Long stemmed blooms of hybrid tea-type form, borne usually one to a stem but on occasion in sprays of 3 to 5 or more. The blooms are held very erect and well above the foliage.

It has a moderate amount of 'fruity' fragrance.

The plant ranges in height from 24 to 36 inches (approximately 60 to 90 cm). The canes are sturdy and erect with moderate branching and medium to heavy foliage covering. The plant is an average to above average bloomer that does well either in the greehouse or outdoors.

The plant has good growth habits, well-shaped and attractive, bearing numerous leaflets of average size.

I have found this variety to be easily asexually reproduced from cuttings.

The seed parent was Futura (U.S. Plant Pat. No. 3,569), and the pollen parent was Party Girl (U.S. Plant Pat. No. 4,598). It differs from its seed parent in the following ways. It is a miniature rose of the light pink class, and Futura is a hybrid tea of the orange-red class. It differs from its pollen parent in the following way. It is a light pink with only a slight base of near Mimosa Yellow, and Party Girl is a yellow blend with predominantly yellow tones and only a slight blush of pink on the margins of the petals.

The descriptive matter which follows pertains to roses grown and color values observed in plants and newly opened blooms in the months of March through August 1986. The plants were grown outdoors in Chula Vista, Calif., and are believed to be accurate standards for this cultivar in similar conditions of soil and climate elsewhere.

The color photograph illustrates the variety.

Referring now specifically to the new and distinct variety of miniature rose plant named 'Sweet Pickins', the following is a detailed description thereof in outline; all major color plate identifications being by reference to the British Colour Council Horticultural Colour Chart, except where common terms of color definition are employed.

2

Type: Hardy, spreading, greenhouse or outdoor, decorative exhibition potted plant.

Class: Miniature.

Variety name: Sweet Pickins.

Flowers borne: Usually one to a stem but on occasion in sprays of 3 to 5 or more on erect stems with foliage well below the blooms.

Quantity of bloom: Moderate to heavy both outdoors or greenhouse grown.

Bud:

*Peduncle.*—Variable in length (25 to 35 mm); average diameter and sturdy; ranging in color from near Scheeles Green (860/3 to 860/2 page 860) to near Lettuce Green (861/3 to 861/2 page 861) with an occasional tinting of bronze.

*Hairs.*—Extremely small and numerous with a reddish color; located over the entire surface of the peduncle and sepals, but not present on the calyx tube.

*Calyx.*—Same color as the peduncle; without hairs.

*Opening.*—Opens well in all weather.

Bloom:

*Size when fully opened.*—Average for a miniature variety (35 to 45 mm).

*Petalage.*—Double; averaging 30 to 35 petals, arranged regularly, plus petaloids (5 to 10 or more).

*Form.*—Urn-shaped to ovoid as the bloom progresses. The petals remain at first somewhat cupped with the apex and/or margins reflexed outward, becoming at maturity more loosely cupped; and the petals reflex more tightly (quilling), until each row of petals forms a five-pointed star.

Petals: Fairly thick with good substance; both the upper and under surfaces of all petals have a matte finish.

*Shape.*—Outer petals are of a very broad obovate form. The intermediate petals are very much like the outer petals only narrower. The inner petals are a broad lanceolate form; and the petaloids are also lanceolate form with some occasional irregularities.

Color: Newly opened flowers from plants grown outdoors (March through August 1986), Chula Vista, Calif.

*All petals.*—Upper Surface — Ranging from near French Rose (520/3 to 520/2 page 520) to near Venetian Pink (420/3 to 420/2 page 420) with a slight base of near Mimosa Yellow (602/3 to 602/2 page 602) and a small tip of near Mimosa Yellow (602/1 to 602 page 602). Under Surface — Ranging from near French Rose (520/2 to 520/1 page 520) to near Venetian Pink (420/2 to 420/1 page 420) with a slight base of near Mimosa Yellow (602/3 to 602/2 page 602) and a small tip of near Mimosa Yellow (602/1 to 602 page 602).

*General color effect.*—Newly opened flowers — Overall pale pink. Three days open — Pink tones fading. Five to seven days — Increased fading of pink tones to near white with some deep pink overlay on the sun-exposed surfaces. Cut blooms at living room temperatures 4 to 7 days or longer.

Reproductive organs:

*Stamens.*—A generous amount arranged uniformly around the pistil.

*Filaments.*—Varying in length with shorter filaments more proximal to the pistil; golden yellow including the anthers.

*Pollen.*—Abundant.

*Pistil.*—Long, abundant and spreading; pale yellow at the base to reddish at the top with pale yellow caps on the styles.

*Ovaries.*—All encased in the calyx.

*Hips.*—Some.

*Seed.*—3 to 5 or more in each hip.

*Sepals.*—Permanent; spear-shaped; open as the bloom opens, recurving against the peduncle, when the bloom is fully opened.

Foliage:

*Leaves.*—Five to seven leaflets on the average; medium size for a miniature rose plant.

*Leaflets.*—Broad ovate-shaped.

*Margin.*—Very serrated with tinting of bronze, especially noticeable on the newer foliage.

*Color.*—Ranging from near Scheeles Green (860/2 to 860 page 860) to near Lettuce Green (861/2 to 861 page 861) with occasional bronzing of the margins which is especially noticeable on the newer foliage. The upper surfaces have a semi-glossy finish, and the under surfaces have a matte finish of a slightly lighter shade than the upper surfaces.

*Rachis.*—Medium strength; upper surface is grooved with very small hairs over the length of it. Under surface has few if any hairs but does contain 3 to 5 small thorns.

*Stipules.*—Varying in length from small to medium; average width; tapering auricles angled outward at about 45 degrees.

Growth:

*Habit.*—Dwarf, bushy; average height for a miniature rose plant (15 to 24 inches).

*Growth.*—Upright and well-branched.

*Canes.*—Ranging from near Scheeles Green (860/2 to 860 page 860) to near Lettuce Green (861/2 to 861 page 861) with some occasional bronzing; medium diameter; sturdy; held erect.

*Main stems.*—Same as Canes.

*Thorns.*—Averaging 12 to 15 per 10 cm on the main stems and fewer on the branches. Reddish in color; small to average in size; slender and straight.

*Branches.*—Color — Same as Canes.

The miniature rose plant and its flowers as herein described may vary in slight detail due to climate, soil and cultural conditions under which the variety may be grown; the present description being of the variety as grown at Chula Vista, Calif.

The following is claimed:

1. A new and distinct variety of miniature rose plant, named 'Sweet Pickins' of hardy, dwarf, bushy, well-branched and attractive in appearance with vigorous growth, substantially as illustrated and described; it is further characterized by its blooms of pale pink, ranging from near French Rose to near Venetian Pink, with hybrid tea-type form that are usually borne one to a stem but on occasion may come in sprays of 3 to 5 or more.

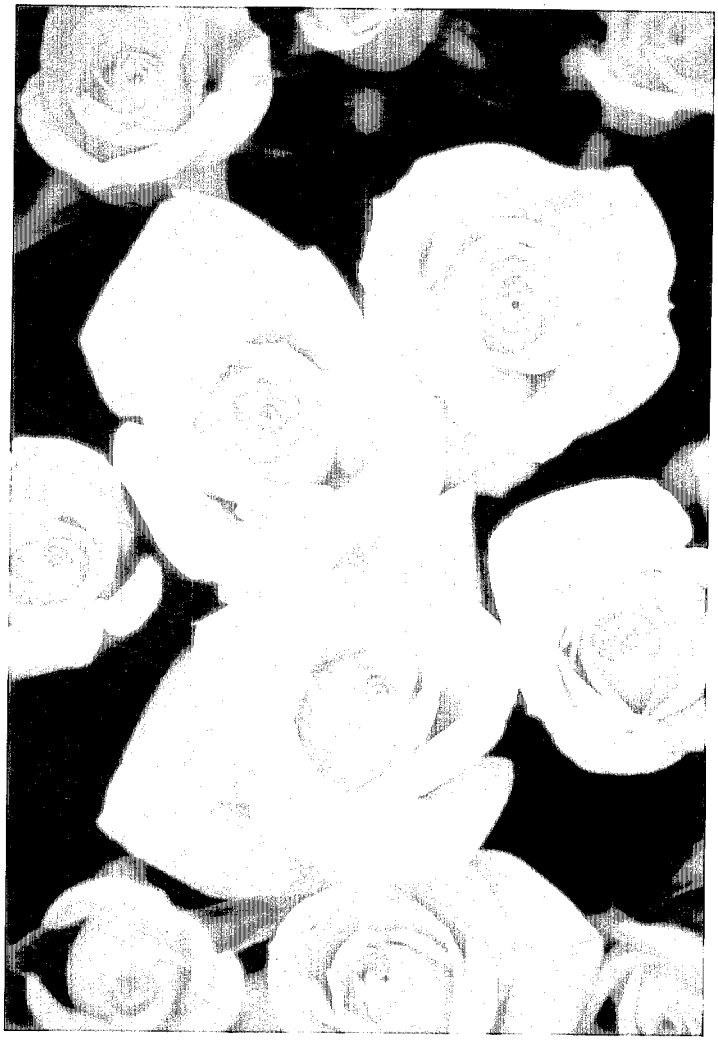

* * * * *